United States Patent [19]

Wilkins et al.

[11] 4,200,493
[45] Apr. 29, 1980

[54] MICROBIAL DETECTION AND ENUMERATION APPARATUS

[75] Inventors: Judd R. Wilkins, Hampton; Glenn E. Stoner, Charlottesville, both of Va.

[73] Assignees: United States of America, Washington, D.C.; University of Virginia, Charlottesville, Va.

[21] Appl. No.: 747,033

[22] Filed: Dec. 2, 1976

Related U.S. Application Data

[63] Continuation-in-part of Ser. No. 641,279, Dec. 16, 1975, Pat. No. 4,009,078, which is a continuation-in-part of Ser. No. 543,860, Jan. 24, 1975, abandoned.

[51] Int. Cl.² ............................................. C12K 1/10
[52] U.S. Cl. ................................... 435/291; 204/1 T; 204/195 B; 435/34
[58] Field of Search ................ 195/103.5 R, 103.5 M, 195/127, 139; 204/1 E, 195 B

[56] References Cited

U.S. PATENT DOCUMENTS 3,403,081  9/1968  Rohrbach et al. ....... 195/103.5 M X

*Primary Examiner*—Raymond N. Jones
*Assistant Examiner*—Robert J. Warden
*Attorney, Agent, or Firm*—Oblon, Fisher, Spivak, McClelland & Maier

[57] ABSTRACT

The presence of microorganisms in a sample is determined by culturing microorganisms in a growth medium which is in contact with a measuring electrode and a reference electrode and detecting the change in potential between the electrodes which arises by the migration and accumulation of said microorganisms adjacent the surface of the measuring electrode thus forming a charge-charge interaction between said measuring electrode and accumulated microorganisms, by measuring the potential change with a high impedance potentiometer.

9 Claims, 13 Drawing Figures

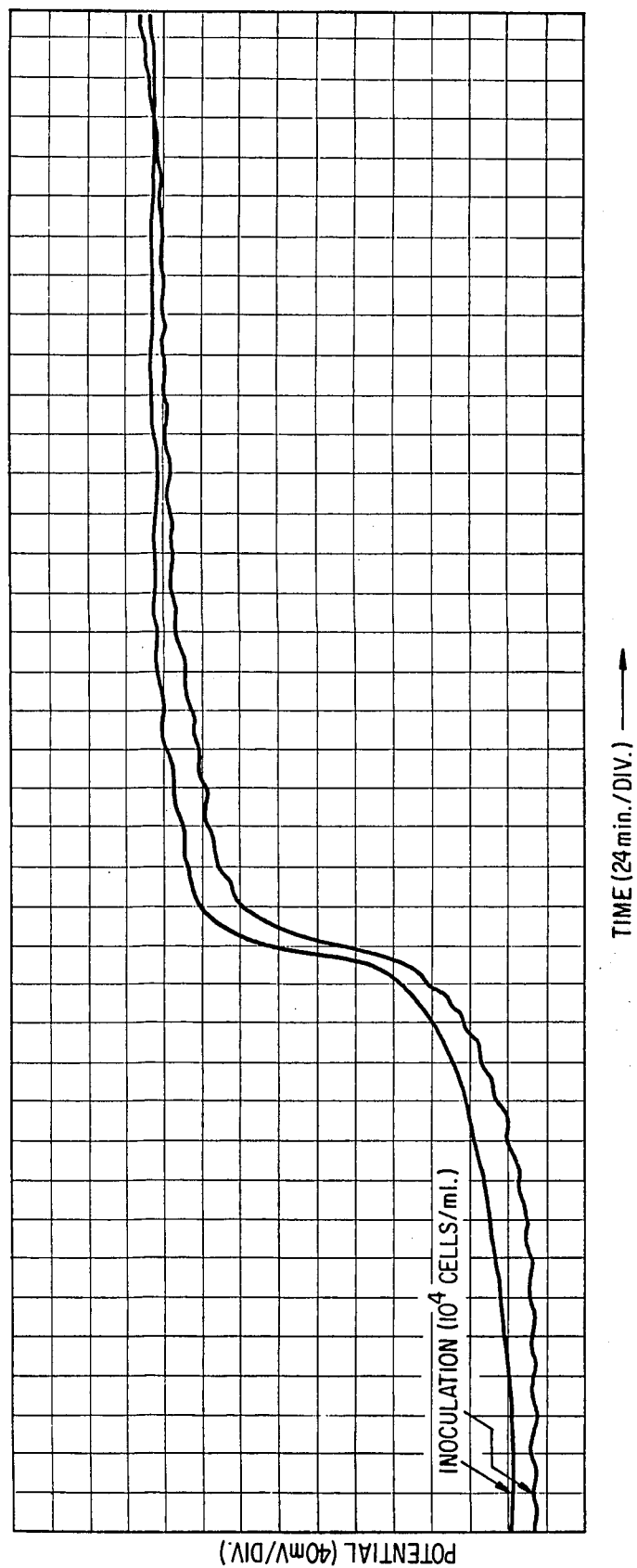

MICROBIAL DETECTION AND ENUMERATION APPARATUS

CROSS REFERENCE TO RELATED APPLICATIONS

This application is a continuation-in-part of application Ser. No. 641,279, filed Dec. 16, 1975 now U.S. Pat. No. 4,009,078 which is a continuation-in-part of application Ser. No. 543,860, filed Jan. 24, 1975 now abandoned.

BACKGROUND OF THE INVENTION

1. Field of the Invention

The present invention relates to a method for detecting microorganisms which may be present in or on any source desired to be tested for the presence of microorganisms. More particularly, the present invention relates to a method of detecting the presence of microorganisms by depositing a source of microorganisms in a cell containing two electrodes, one of which is protected from exposure to the microorganisms and a nutrient medium and detecting the change in potential between the measuring electrode exposed to the growing microorganism and the reference electrode.

2. Description of the Prior Art

Presently, several methods are known for the detection of microorganisms which may be present in various sources which include aqueous media such as blood, plasma, fermentation media and the like. The methods are generally divided into two classes of detection in which the first is a screening test to determine whether or not large numbers of microorganisms are present in a sample. If a positive test is obtained by the first step, a second level of testing is employed to determine the type and amount of organism present. Most commonly, methods which establish both the identity and amount of microorganism are based upon a sequence of steps of culturing, growth and observation of the microorganism. Growth rates are observed in the culture which are derived from multiple dilutions of the same sample. By observing the time at which the diluted samples reach observable populations, the concentration of microorganisms in the original samples can be estimated.

The estimation of microorganism populations is most generally accomplished by one of three techniques. The first technique is a nutrient agar plating technique in which a microorganism is allowed to grow on an agar nutrient substrate and the growth of the microorganism is initially observed visually and thereafter by microscopic observation. This is the most common method in use clinically.

The second type of technique includes several methods which can be classified as chemical methods. One method of analysis involves supplying a microorganism in a growth medium with carbon-14 labeled glucose. The microorganism metabolizes the radioactive glucose and evolves $C^{14}O_2$, which is sampled and counted. While positive results can be obtained by this method in a relatively short period of time, the method is encumbered by various operational complexities, is expensive and is hazardous from the standpoint of the necessity of handling radioactive samples. Another analytical method of determining the type and amount of bacteria present in a sample is based upon the chemiluminescent reaction between luciferase and luciferin in the presence of ATP. Bacteria are grown on a culture and then the cells are lyzed to free the ATP present therein. The liberated ATP reacts with the luciferase-luciferin combination whereby chemiluminescent light is emitted which is detected by a photomultiplier and used to determine the amount of the organism present. The principal disadvantage of this technique is the expense of the materials involved in the reaction. Still another chemical method involves a measurement based upon the metabolic conversion of nitrite ion to nitrate ion. This method, however, is only applicable to some bacteria and yeasts.

The third type of technique used for the detection of microorganisms involve non-chemical methods. One method involves the evaluation of relatively clear microorganism suspensions by modified particle counters. However, the method is non-specific and does not provide a distinction between viable microorganisms and dead ones, or even non-biologic particulate matter. A second method involves the detection of microorganisms by impressing an alternating current across a pair of electrodes which have been placed in a microorganism containing medium and observing the change in impedance of the current as a function of the growth of the microorganism. This technique however, is apparently not as amenable to automation as has been expected for the device and method.

A bio-chemical sensor is known as disclosed by Rohrback et al U.S. Pat. No. 3,403,081, which is used to detect trace elements and poisons in liquid and gaseous media. The sensor is constructed by placing a measuring electrode such as an inert wire gauge cylinder of nickel, platinum, stainless steel or the like upon which is impegnated a colony of a microorganism or an enzyme and a reference electrode such as the standard Calomel electrode in an electrolyte. The leads from each electrode are attached to a voltmeter. The oganism or enzyme impregnated or in close proximity to the measuring electrode generates a current within the cell by causing chemical reactions at the surface of the electrode or by promoting chemical reactions to produce materials which in turn provide depolarization reactions at the electrode. The device functions by admitting a trace element or a poison into the device which deactivates the enzyme or kills or deactivates the microorganism thus causing a change in the potential difference between the electrodes which is detected by a change in the voltmeter readings. Considering the fact that the enzyme or microorganism promotes or causes a considerable chemical reaction at the measuring electrode which is detected by a standard voltmeter in the circuitry of the cell, the current generated within the cell must be substantial. The electroanalytical device of the present invention which is used to determine the type and amount of a microorganism in a solution, on the other hand, does not require the impregnation of a sizable colony of a microorganism on the measuring electrode but rather operates by detecting a microorganism in solution which gradually concentrates about the measuring electrode. A further critical distinction between the method and apparatus of the present invention and the method of the reference is that the circuitry of the present system must contain a high impedance potentiometer and not the conventional voltmeter used in the reference's process, because the present system is dependent upon the measurement of an electrostatic-like potential difference between the measuring electrode and the microorganism in solution. If a standard voltmeter were used in the circuitry of the present invention, far too much current would be drawn by the voltmeter which would destroy the relatively delicate electrostatic-like potential difference between the measuring electrode and the microorganism concentrated about the electrode's surface.

Consequently, a need continues to exist for a method of rapidly, automatically and economically determining types and amounts of various microorganism by a conceptually simple and economic technique.

SUMMARY OF THE INVENTION

Accordingly, one object of the present invention is to provide a method which is amenable to the rapid and automatic detection of the amount and type of viable microorganism present in a fluid medium such as blood samples, polluted water and fermentation liquids by electroanalytical means.

Another object of the invention is to provide an electroanalytical means for determining the type and amount of microorganism in a fluid medium such as blood samples, plasma samples, polluted water and the like by potentiometrically measuring the potential change generated in a cell containing a measuring and a reference electrode through the difference in potential between the two electrodes.

Yet another object of the invention is to provide several types of electroanalytical cells equipped with a measuring-electrode and a reference electrode and a nutrient for the growth of microorgansms which are capable of easily and economically allowing the measurement of the voltage change generated at the measuring electrode by the difference in potential between the measuring electrode and the reference electrode caused by the presence of the microorganism in the fluid medium.

Yet another object of the present invention is to provide a high impedance voltage measuring device so that the above mentioned potential change can be measured or recorded without the passage of current.

Briefly, these objects and other objects of the present invention as hereinafter will become more readily apparent can be attained by a method for determining the presence of microorganisms in a sample by culturing microorganisms in a growth medium which is in contact with a reference electrode and a measuring electrode and detecting the change in potential between the electrodes which arises by the migration and accumulation of said microorganism adjacent the surface of the measuring electrode thus forming a charge-charge interaction between said measuring electrode and accumulated microorganisms, by measuring the potential change with a high impedance potentiometer.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings; wherein:

FIG. 1 shows a potential response curve for the growth of Pseudomonas versus time in 10 ml of Trypticase Soy Broth medium;

DETAILED DESCRIPTION OF THE PREFERRED EMBODIMENTS

Figure 12:
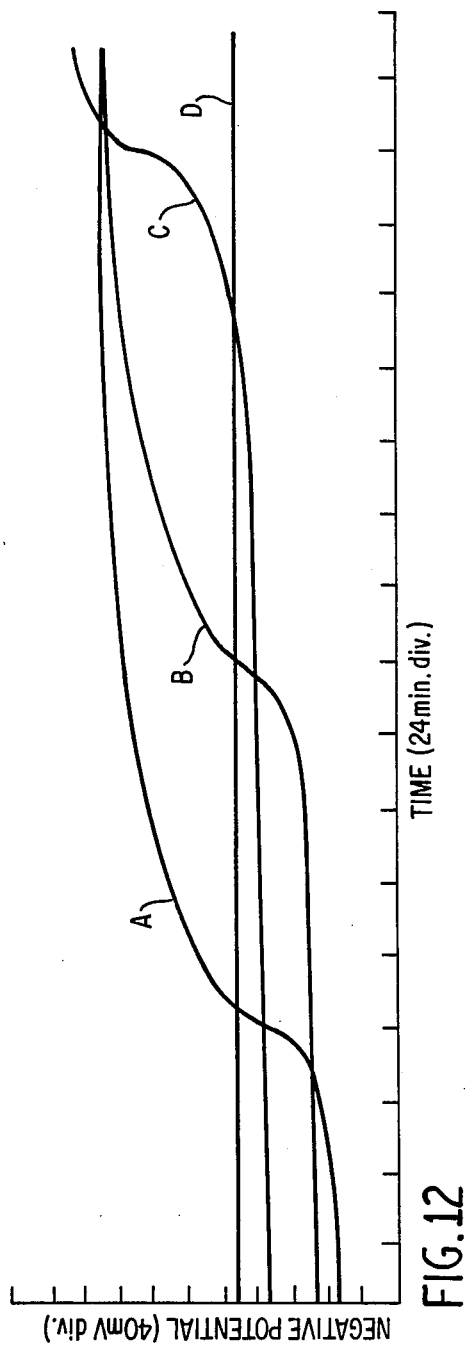
FIG. 12 shows several potential versus time curves which show the growth impeding influence of the antibiotic, ampicillin, on $S.$ $epidermidis;$

The discovery upon which the method and apparatus of the present invention is based is that the presence of certain population levels of a given microorganism in a fluid medium confined in a cell containing a measuring electrode and a reference electrode generates potential changes within the cell because of a difference in electrostatic charge between a live organism and the measuring electrode. The potential is measured by a high impedance potentiometer which is fastened through conductive leads to the electrodes of the cell. It has been found that all microorganisms exhibit a relatively negative electrostatic charge in solution versus the electrode which is used as the measuring electrode which consequently renders all microorgansms amenable to detection by the method of the present invention. It is believed that the growing microorganisms gradually migrate to the exposed surface of the measuring electrode which is somewhat positive relative to the microorganisms. In order that a potential difference exist between the measuring and reference electrodes, it is essential that the reference electrode either only contact the growth medium and not the microorganisms or not be sensitive to the microorganisms's charge and that the microorganisms concentrate themselves about the measuring electrode. For example, when a metal wire or the like is used as the reference electrode, the electrode is normally shielded from the microorgnisms by a fluid permeable but organism impermeable substance. When a device such as the calomel electrode is used as the reference electrode, it is normally protected by the glass envelope from the microorganisms. The accumulation of microorganisms about the measuring electrode alters the potential of the measuring electrode relative to the reference electrode and consequently, a change in potential is set up between the electrodes because of the charge-charge interactions at the measuring electrode. The voltage change generated by this electrostatic interaction is the means by which the presence of microorganisms in solution can be detected.

The cell structure which confines the growing microorganisms and to which the electrodes are attached can be manufactured from any convenient materials normally used in the manufacture of electroanalytical cells such as glass, plastic and the like. Any material which is suitable for such use and which does not interfere with the growth or viability of the microorganisms and does not affect the voltage generated within the cell can be used.

The electroanalytical cell is provided with a culture medium for the growth of the microorganisms placed within the cell. Any culture medium which is commonly used for the growth of microorganisms can be used, and therefore, the type of culture medium used in not critical. Suitable growth media include brain-heart infusion, trypticase soy broth (TSB), phenol red broth base +1% glucose, trypticase soy broth +$CO_2$, milk, beer, sodium glycolate and the like. The amount of growth medium provided within the measuring cell, of course, is not critical.

The measuring and reference electrodes attached to the cell can be made of the same conductive material or they can be of different materials. Usually, the measuring electrode is fabricated of any suitable electrode material in any convenient form and is attached to the cell so that a portion thereof is in contact with the liquid medium within the cell. Suitable materials from which the measuring electrode can be fabricated include the noble metals such as silver, platinum, palladium, gold, and the like, tungsten, molybdenum, nickel and the like, and various metal alloys such as stainless steel, nickel-chromium, and silver-palladium. The form of the electrode is not critical and can be of any suitable shape such as a wire, ribbon, coil or the like.

The reference electrode can be fabricated of any of the suitable electrode materials used for the measuring electrode. Thus, conceivably the reference electrode can be of the same material as the measuring electrode, which is a most unusual electrode configuration for galvanic cells. Normally, the electrodes employed in galvanic cells are fabricated of different materials in order to have an operable cell. The reference electrode is also attached to the cell by any convenient means in a manner such that a portion (such as one end of a wire or ribbon) of the electrode is in contact with the liquid medium in the cell. The portion of the reference electrode in contact with the medium is usually shielded from contact with the microorganisms in the medium. When the measuring and reference electrodes are of unlike metals or alloys, it is not necessary to shield the reference electrode since the microorganisms will preferentially accumulate about the more positive of the two electrodes in the cell. On the other hand, when the measuring and reference electrode are the same material, the reference electrode must be shielded. Any means by which the reference electrode can be shielded from the growing microorganisms but at the same time allows contact with the liquid medium can be used. Thus, for example, the exposed portion of the electrode can be embedded within a gel such as an agar gel, gelatin, dextran gel, carrageenan gels—acrylimide and the like. Membranes such as relatively large pore ultrafiltration membranes or even large pore membranes, frit, ceramic or porous films of plastic are all suitable if they are impermeable to the microorganisms. If the reference electrode and the measuring electrode are fabricated of the same material such as two stainless steel electrodes which is a preferred embodiment of the invention, two platinum electrodes or the like, the potential change generated at the sensing electrode cell is relatively free of thermocouple effects. That is, if the electrodes are the same, no voltage will be generated which is attributable to thermocouple effects. If the electrodes are fabricated of unlike metals or metal alloys, then the thermocouple effect can exist and the potential readings obtained should compensate for that portion of voltage attributable to the thermocouple effect. Thus, it can be appreciated that the thermocouple effect which can arise with certain electrode combinations is not critically restrictive and one operating according to the present method need only be aware of this factor.

The reference electrode besides being of the type described above, can also be a standard reference electrode such as one of the standard calomel electrodes or the mercury-mercurous sulfate electrode, the Ag/AgCl electrode, or the quinhydrone electrode. If one of these standard types of reference electrodes is used, the portion of the electrode within the liquid medium in the cell need not be shielded from the microorganisms, because either the construction of these electrodes in a glass envelope normally eliminates contact of the interior working portions of the electrode with the microorganisms in solution or they have a potential which is not effected by microorganisms.

In order to measure the voltage generated within the electroanalytical cell containing the growing microorganism, it is necessary to connect both electrodes of the cell to a high impedance potentiometer. The type of potentiometer used is not critical with the only requirement being that it be of the high impedance type. The potentiometer must have an imput impedance over the range of $10^7$ ohms to $10^{10}$ ohms, preferably greater than $10^8$ ohms. If a relatively low impedance potentiometer is used, too much current would be drawn through the measuring device thus upsetting the charge-charge interaction between the measuring electrode and the microorganisms. With the destruction of the electrostatic potential at the electrode, no potential readings can be obtained. Of course, other apparatus accessories compatible with the high impedance potentiometer such as an amplifier and a recording device can also be added to the instrumentation package.

In the performance of a measurement according to the procedure of the present invention, a sample of a microorganisms is introduced into the growth medium within the cell. In one embodiment, a fluid sample of a microorganism can be injected into the cell through a self sealing cap which seals the cell to the atmosphere or is drawn into the cell under force of vacuum. Microorganisms can also be introduced into the cell in the form of a gaseous sample with the stipulation that the microorganisms are introduced into the growth medium of the cell. A basic feature of the present technique is that a stable baseline can be established by the recording instrument which is attached to the high impedance potentiometer and which plots changes in potential as a function of time before the minimum detectable concentration (MDC) of the growing microorganism is attained. In other words, the stable baseline is equivalent to a value of zero for the function of dE/dt. Growth of the microorganism occurs and once the population level reaches the minimum detectable concentration normally of about $10^5$ organisms/1 ml for all except the slower growing microorganisms, the microorganism can be detected by the voltage generated. The voltage as measured in millivolt readings always changes in a negative direction. This is because the charge on the microorganisms is more negative than that on the measuring electrode. For slow growing microorganisms such as the bacillus of tuberculosis, however, the lower detectable concentration can be as low as $1 \times 10^3$ organisms/1 ml. In instances where the method of the invention is used to detect slow growing microorganisms, the cell can be agitated by shaking, for instance, or by any other suitable means. Agitation of the microorganisms containing solution facilitated growth of the microorganisms in some cases and may thus reduce the delay time for the detection of the microorganism. However, since the present invention requires a net accumulation of organisms at the measuring electrode in order to have the necessary electrical charge-charge interactions, too vigorous stirring may sweep the microorganisms away and eliminate the potential change. The temperature range over which the microorganisms are grown and eventually detected span the range of 15° to 60° C., preferably 32°-37° C. Pressure is not a critical factor in the measurements since growth and detection of the microorganisms can occur under partial vacuum conditions as well as under super-atmospheric pressures. Thus, for instance, the method of the present invention is amenable to the detection of microorganisms which grow under pressure as in the manufacturing of beer.

The method of the present invention can be used to successfully detect any type of microorganism which can be cultured in the nutrient medium provided within the electroanalytical cell or added to the cell in a suitable concentration. Also it is not absolutely necessary for the microorganisms to be growing or metabolizing provided they remain alive. This is because it is their viability that gives them their negative charge, which they loose at death. Thus, the method is applicable to the detection of yeasts, fungi and bacteria. Specific examples of bacteria which can be detected by the method of the present invention include the non-hydrogen producing bacteria, *Staphylococcus aureaus, Staphylococcus epidermidis, Streptococcus, Listeria monocytogenes, Pseudomonas aeruginosa. Moraxella, Shigella alkalescens, Diplococcus pneumoniae, Bacillus subtilus,* and *Hemophilus, influenzae.* Suitable examples of yeasts which can be detected include *Candida* species such as *Candida albicans* and *Candida rugosa, Hansenula* species such as *Hansenula anomala, Pichia* species such as *Pichia membranaefaciens, Torulopsis* species and *Saccharomyces cerevisiae.* Suitable examples of fungi include the various species of *Aspergillus* such as *Aspergillus auricularis, A. barbae, A. bouffardi, A. calvatus, A. concentricus, A. falvus, A. fumigatus, A. giganteus, A. glaucus, A. gliocladium, A. mucorodies, A. nidulans, A. niger, A. ochraceus, A. pictor,* and *A. repens* and the species of the large group of fungi known as *Fungi Imperfecti.*

A number of bacteria form a class of bacteria which are known for their ability to release hydrogen during their growth. These bacteria include *Escherichia coil, Enterobacter aerogenes, Serratia marcescens, Proteus mirabilis, Citrobacter intermedium, Gitrobacter freundii,* *Salmonella* and and *Klebsiella.* Since these bacteria migrate toward the measuring electrode as all microorganisms do, their release of hydrogen tends to concentrate about the measuring electrode. The presence of hydrogen at the measuring electrode very substantially amplifies the characteristics of the electrode such that it becomes similar to the well known hydrogen electrode. Thus, in effect a completely different type of measuring electrode exists for the measurement of hydrogen producing organisms than for non-hydrogen producing organisms. The principle behind the operation of the hydrogen electrode is that the following equilibrium exists at the surface of the metal electrode, usually platinum or gold:

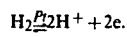

$$H_2 \rightleftharpoons 2H^+ + 2e.$$

It is clear from this expression that an equilibrium exists between molecular hydrogen and hydrogen ions in solution and it is the variations within the equilibrium that determines the potential of the electrode. Once an equilibrium has been established at the electrode surface, the electrode is termed as a "nonpolarizable" or reference electrode. The normal hydrogen (reference) electrode is platinum in an acid solution of pH=0 with a saturated solution of molecular hydrogen at a defined temperature. The normal hydrogen electrode (NHE) is defined to have a potential of 0.00 volts and forms the relative basis for the potential scale of all other electrode reactions as well as establishes the basis for the electromotive series of metals.

In a more specific aspect of the measurement of hydrogen producing bacteria a calomel electrode is used as the reference electrode in combination with a metal measuring electrode. The calomel electrode has a potential of about +0.23 volts with respect to NHE and since the growth medium has a pH of about neutral or 7, the measuring hydrogen electrode has a potential of about −0.42 volts with respect to NHE. Thus, the measuring electrode for hydrogen producing bacteria has a potential of about −0.65 volts; i.e. $(-0.42)-(+0.23)=-0.65$ in a negative direction relative to calomel. Because, in reality a pressure of one atmosphere of hydrogen is never achieved at the measuring electrode because of atmospheric dilution effects due to $CO_2$, nitrogen and the like, a leveling-off potential of approximately −0.4 to −0.5 volts versus calomel is achieved in the measurements obtained for hydrogen producing bacteria.

In the measurements of both hydrogen and non-hydrogen producing microorganisms, a lag time is initially observed from the time the analytical cell is inoculated with the microorganism until the time the microorganism reaches sufficient population levels to be detected. Thereafter, the potential continues to increase in a negative direction until a peak potential is attained where the potential levels off. Thereafter, with advancing time the potential drifts back to more positive potentials. For non-hydrogen producing microorganisms, the total change in millivolt readings ranges from about 200-300 millivolts. In the case of hydrogen producing organisms, the initial negative increases in potential are attributable to the presence of the organism only. Thereafter, as the effects of the hydrogen build-up at the electrode become significant, the potential sharply increases to significantly more negative potentials than are obtained for non-hydrogen producing microorganisms. The negative increase in potential attributable to the presence of hydrogen at the measuring electrode amounts to about 500 millivolts.

The potential readings obtained for each measurement represent the sum of the change in potential caused by the presence of the microorganism in solution and the potential changes attributable to other solution and system factors which cause minor changes in the potential. These factors are characteristic of the particular liquid medium present in the cell as well as the electrodes used and should be ascertained by a potential reading of the medium free of the presence of detectable amounts of particular microorganism to be tested. By achieving a measure of this background potential, one therefore can readily determine that the total potential change is caused by the presence of the microorganism. An interesting embodiment of the present invention is that it affords a method of detecting a mixture of microorganisms in a sample desired to be tested. When a sample containing a mixture of 2 or more types or species of microorganisms is cultured within the analytical cell, the microorganism which reaches its minimum detectable limit first is the one which will be detected by the system. With this knowledge, it is therefore apparent that the skilled artisan can alter the growth conditions such as temperature and the type of culture medium to favor the growth of one type of microorganism to the detriment of other microorganisms and thus preferentially detect one microorganism over another. For example, in order to detect fecal coliform in a mixture of microorganisms, the temperature of the growth medium can be raised to preferentially kill the other microorganisms so that only the coliform remains.

The volume of the liquid medium within the electroanalytic cell is not critical. Of course, the liquid medium must be in ionic contact with both electrodes. The volume of the liquid growth medium can be any reasonable size which the skilled artisan can readily determine. Of course, as the volume of the liquid is increased, the greater the dilution of the microorganism, and the lower the resulting response obtained. It will be appreciated that the sealed electronanalytical cell can contain a growth medium therein prior to introduction of the microorganism or the growth medium and sample of microorganism can be introduced into the cell at the same time. The quantity of microorganisms introduced into the cell is not critical and need not be within any set limits.

A further understanding of the method of the present invention can be achieved by reference to FIG. 1 which shows two simultaneous potential versus time recordings of a *Pseudomonas aeroginosa*, initial inocula $10^4$ cells/ml sample cultured in a trypticase soy broth medium at 37° C. over a period of several hours, in two separate electroanalytical cells. Each curve shows the potential response of the organism as a function of time. For the first hour or two the chart shows no significant response. Thereafter, the organism begins to reach minimum detectable concentrations as evidenced by the gradual increase in the potential reading in both cells. The curve then begins to recede gradually after reaching its peak value due to the eventual death of some of the cell population.

The invention thus far has been described in terms of directly measuring the presence of living microorganisms in an electrochemical cell. In another embodiment of the invention, substances or events can be monitored which change or destroy microbial viability such as exposing the microorganisms in the cell to an antibiotic, serum antibodies, chemical toxins, viruses, e.g. bacteriophage, or any other anti-microbial or anticellular event. Thus, the effect of an anti-microbial agent or event can be monitored by two methods:

(1) by adding antimicrobial agent to standard dilutions of cultures at some concentration prior to reaching the MDC: and (2) by adding the anti-microbial agent at or above the MDC.

The method of the present invention is therefore useful in antimicrobial susceptibility testing for the investigation of the activity of new anti-biotics, or in the surveillance of developments in an organism such as the development of antibiotic resistance by the organism. Most importantly, in vitro evidence of bacterial-antibiotic interactions enables a clinician to predict the in vivo efficacy of a particular drug. The present method is useful in antimicrobial suscpetibility testing when the causative organism doesn't respond predictably to antibiotics as shown in Table 1 below, and also when the organism is invariably susceptible to a particular drug as shown in Table 2 below.

TABLE 1

MICROORGANISMS WITH UNPREDICTABLE ANTIMICROBIAL RESPONSE

| Organism | Agent to which organism may be sensitive |
|---|---|
| Staphylococcus aureus | Penicillin G., methicillin, cephalothin, vancomycin |
| Escherichia coli | Ampicillin, cephalothin, tetracycline, chloramphenicol |
| Klebsiella pneumoniae | Cephalothin, tetracycline, kanamycin, chloroamphenicol |
| Pseudomonas aeruginosa | Gentamycin, tobramycin, carbenicillin, polymixin B |
| Proteus mirabilis | Penicillin (moderately resistant) ampicillin, kanamycin |
| Proteus vulgaris | Tetracycline, kanamycin, chloramphenicol |
| Enterobacter aerogenes | Tetracyclines, chloramphenicol kanamycin |
| Salmonella | Ampicillin, tetracycline, cephalothin, kanamycin |
| Shigella | Same as above (Salmonella) |
| Listeria monocytogenes | Penicillin G, erythromycin, chloramphenicol |

TABLE 2

MICROORGANISMS WITH PREDICTABLE ANTIMICROBIAL RESPONSE

| ORGANISM | AGENT TO WHICH ORGANISM IS UNIFORMLY SENSITIVE |
|---|---|
| Neisseria gonorrhoeae | Penicillin G, erythromycin |
| Diplococcus pneumoniae | All penicillins, cephalothin erythromycin, vancomycin |
| Streptococcus pyogenes | Same as Diplococcus |
| Clostridium perfringens | All penicillin, cephalothin, tetrayclin |
| Haemophilus influenzae | Penicillin G, ampicillin, tetracycline, chloramphenicol |
| Haemphilus pertussis | same as H. influenzae |
| Brucella | Tetracycline |
| Corynebacterium diphtheria | Erythromycin, penicillin G |
| Neisseria meningitidis | Penicillin G, ampicillin |

Figure 2:
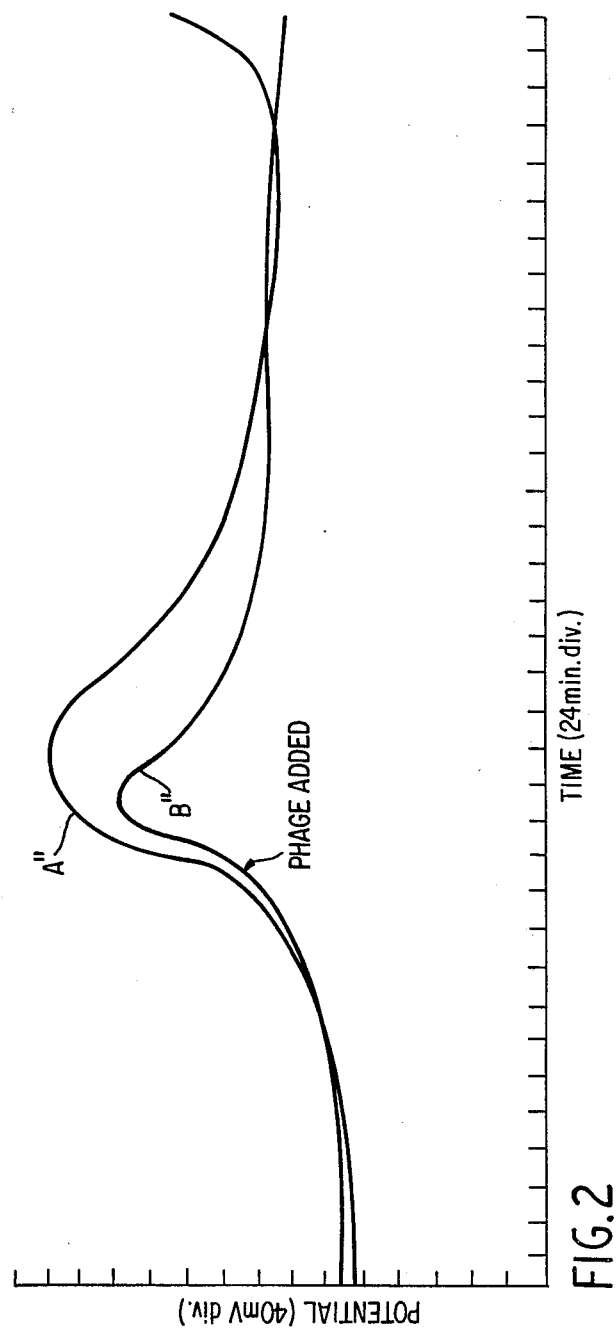
FIG. 2, shows two potential versus time curves which demonstrate the growth impeding influence of bacteriophage on bacterial strains of $E.$ $coli;$

FIG. 2 shows another example of an agent which disrupts the growth of a microorganism. Curves A" and B" show the potential-time responses for the growth of a strain of *E. coli* in a growth medium, wherein different concentrations of bacteriophage $\phi_x$, i.e. $10^4$ phage/ml and $10^5$ phage/ml respectively were added to the growing microorganism after the MDC was reached. The time required for the potential to reach its peak after the virus is added is inversely related to the logarithon of the virus concentration at the time of addition, i.e.

$$\log C \text{ virus} \propto \frac{1}{\tau\text{peak} - \tau MDC}$$

By this technique the analysis of viral concentration in less than one hour can be achieved.

Figure 3:
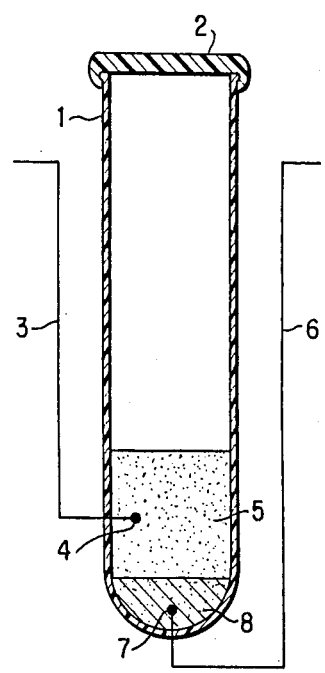
FIG. 3, is an embodiment of one form of the electroanalytical cell of the present invention.

The following drawings represent various embodiments of the electroanalytical cell of the present invention:

FIG. 3 shows an embodiment of an electroanalytical cell in which chamber 1 is sealed with a resilient cap 2 which is self sealing. Measuring electrode 3 is attached and secured to the chamber through an opening (not shown) in the chamber wall. Portion 4 of electrode 3 extends through the chamber wall so that its surface is exposed to culture medium 5 in the chamber through an opening (not shown) in the base thereof. The portion 7 of the reference electrode within the chamber is shielded from any microorganism which is present within the culture medium by shielding means 8. Shielding means 8, measuring electrode 3 and reference electrode 6 can be formed from the materials described above. In the use of the above described device, an appropriate quantity of a microorganism containing fluid sample is injected into the chamber through the cap. The exterior terminals of the measuring and reference electrodes are then attached by leads to the appropriate terminals of a high impedance potentiometer and the medium is monitored as the microorganism grows.

Figure 4:
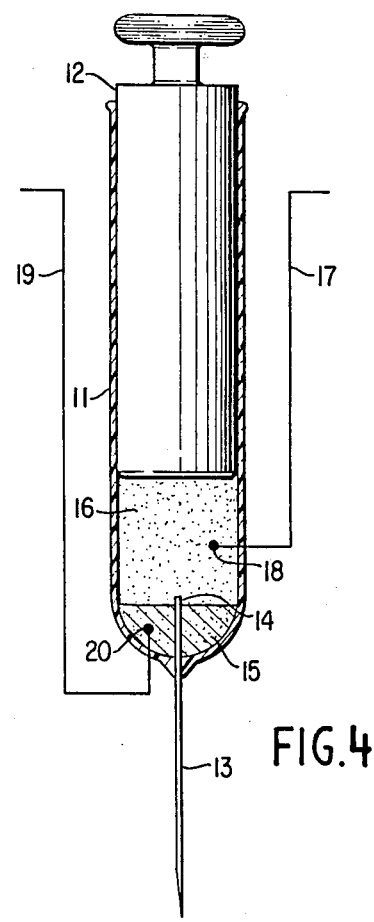
FIG. 4, is another embodiment of the electroanalytical cell of the the present invention wherein the cell has been adapted to function in part as a syringe.

Another embodiment of the electroanalytical cell of the present invention is shown in FIG. 4. In this device, the cell is essentially a syringe of chamber 11 and plunger 12. The base of the chamber is provided with a suitable hollow conduit 13 which can be a hollow needle, rubber tube, or the like, one end 14 of which protrudes through the chamber and microorganism shielding means 15 into the bulk of the culture medium 16 within the chamber. The device is equipped with measuring electrode 17 which is attached to the chamber through an opening (not shown). Portion 18 of the electrode is in contact with the culture medium. Reference electrode 19 is attached and secured to the base of the chamber through an opening (not shown). That portion of the electrode within the chamber 20 terminates within shielding means 15.

The device of FIG. 4 is adapted so that the same device can be used to directly withdraw or expel fluids from a living body into a culture medium and be immediately attached to a potentiometer so that the growth of any microorganism present in the body fluid can be monitored.

Figure 5:
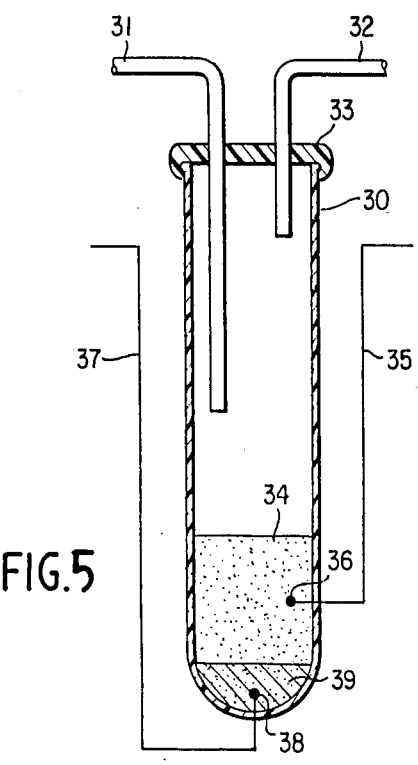
FIG. 5 is an embodiment of the device of the present invention wherein the chamber of the device is equipped with means for drawing a microorganism containing fluid sample into the device under force of vacuum.

Yet another embodiment of the cell of the present invention is shown in FIG. 5. The device in this case is adapted so that a fluid containing a microorganism to be analyzed can be withdrawn into chamber 30 through entry line 31 via a vacuum applied to vacuum line 32. Both lines are shown as protruding through resilient sealing cap 33, however, it can be appreciated that both lines could be attached to the device through the walls of chamber 30 if desired. As the fluid sample is drawn into the device by the force of the vacuum, it falls upon and is mixed within culture medium 34. Measuring electrode 35 is attached to the device through an opening (not shown) so that the measuring end of the electrode (36) protrudes into the culture medium. Reference electrode 37 is attached to the device in a similar manner at the base of the chamber so that the end 38 within the chamber projects into a shielding means 39 which shields the end of the electrode from microorganisms in the culture medium. The device can be used in the same manner as the device under a force of vacuum rather than by injection through the sealing cap.

Figure 6:
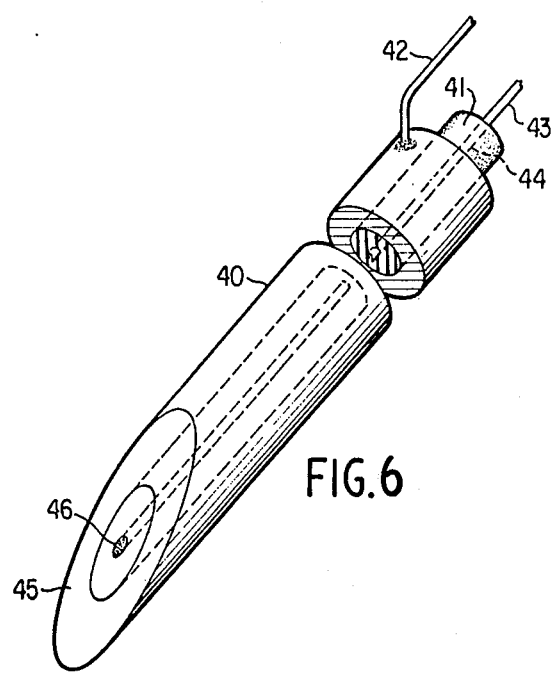
FIG. 6 is an embodiment of the device of the present invention which in part is a needle suitable for the sampling of body fluids.
Figure 7:
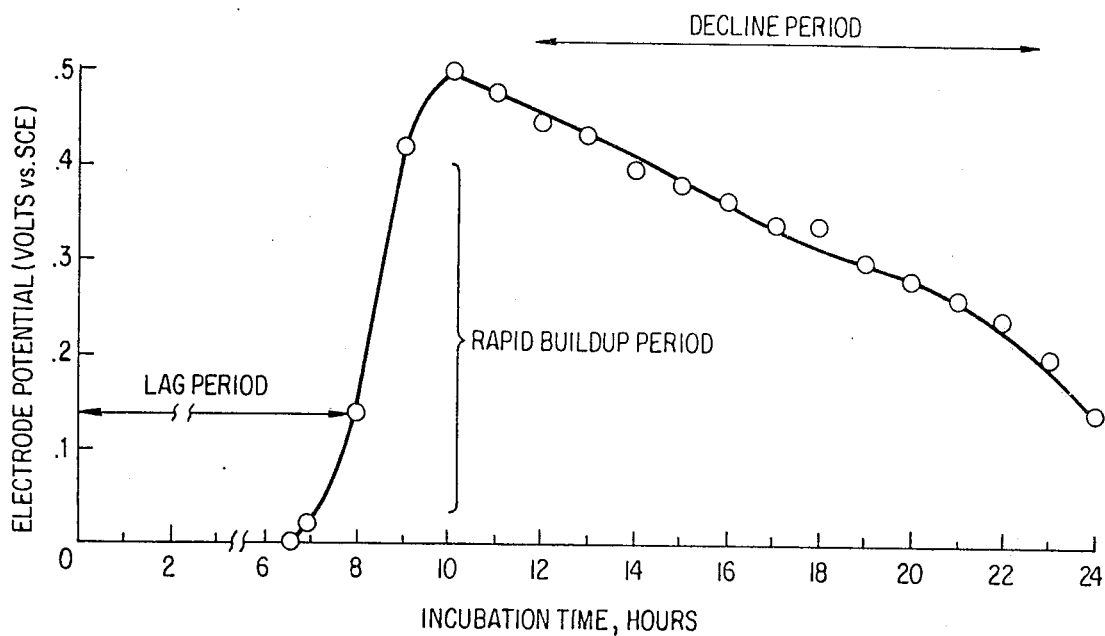
FIG. 7 is a strip chart recording of potential versus time for the culturing of $E.$ $coli;$
Figure 9:
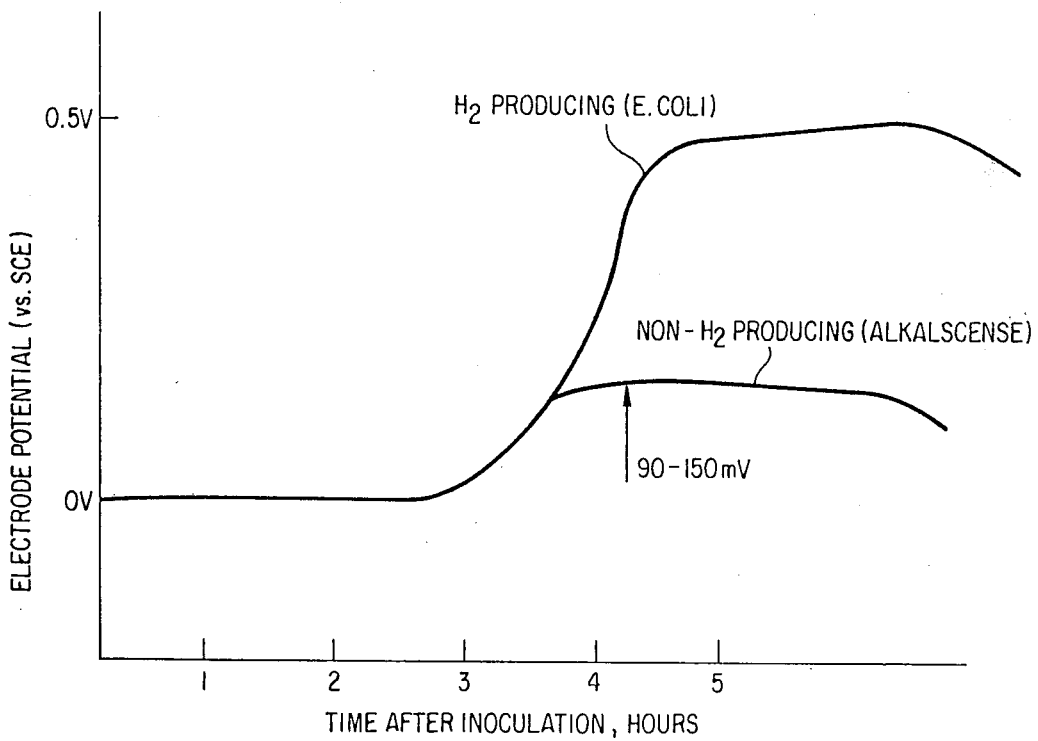
FIG. 9 shows a comparison plot of potential versus time for a hydrogen producing organism ($E.$ $coli$) and a non-hydrogen producing organism(alkalescens)

In still another embodiment of the device of the present invention, as shown in FIG. 6, the functioning parts are present within a needle. Thus, the device is fabricated of a conduit 40 which can be a hollow needle inside of which is concentrically disposed electrically insulating means 41. Lead 42 is attached to the exterior surface of the needle so that it functions as the measuring electrode. Wire 43 is disposed within the hollow inner core 44 of the insulating means and attached at the base of the insulating core 45 by a shielding means 46. The needle apparatus is then attached to an evacuated, sealed chamber (not shown) which can contain a growth medium. When used, the needle is injected into a subject and fluids containing the microorganism desired to be measured are withdrawn. The leads attached to the needle can then be attached to a high impedance potentiometer to measure the microorganisms in the fluid.

In another embodiment of the device of the present invention (not shown), the device of FIG. 3 can be sealed or packed under a vacuum to provide a vacuum within the device. The base of the chamber of the device is provided with a sealed hollow needle whose attached end projects through the base and shielding means into the culture medium. The device can be used to withdraw a fluid containing a microorganism into the chamber by simply injecting the free end of the needle into the body of an animal for instance, whereby the force of the injection and/or the fluid pressure breaks the seal within the needle and the fluid is withdrawn into the device by the force of the vacuum.

The present invention enjoys a wide variety of fields of application, because the present invention is applicable wherever it is desired to detect the presence and quantity of microorganisms in a sample. Thus, the present invention can be used to detect the presence of bacteria in a biological or non-biological fluid medium. The method of the invention can be used as an antibiotic screening technique to determine the effectiveness of an antibiotic. For example, a microorganism can be cultured in a cell and an antibiotic added thereto. The medium would then be observed to detect the influence of the antibiotic on the potential readings obtained. Biological applications include the detection of microorganisms in such body fluids as urine, blood, cerebrospinal fluids, sputum, amniotic fluid, synovial fluid, plasma and artifical kidney dialysate. The present technique is also amenable to throat tissue cultures, vaginal and cervical tissue cultures and tissue biopsies. The present technique finds further application for the detection of microorganisms in alcohol producing media such as from wood, grain, molasses, sulfite and waste liquors; from the production of wine and beers and from the production of glycerol. Still another area of application is in the fermentation of organic acids such as lactic acid, citric acid, fumaric acid and acetic acid. Yet another general area of applicability is the food processing industry, particularly in the packaging of and the production of beverages and canned goods. Still further areas of applicability include rural, city and regional water supplies, water holding tanks and septic tanks.

Having generally described the invention, a further understanding can be obtained by reference to certain specific examples which are provided herein for purposes of illustration only and are not intended to be limiting unless otherwise specified.

EXAMPLE 1

For the specific experimental procedure described below, the following hydrogen producing bacteria were obtained from the American Type Culture Collection (Rockville, Maryland):

*E. coli* (12014), *E. aerogenes* (13046), *S. marcescens* (13880), *C. intermedium* (6750), *C. freundii* (8090), and *P. mirabilis* (12453). Cultures were maintained at 5° C. on trypticase soy agar slants (TSA, BBL) and transferred monthly.

Inoculum preparation, viable counts, and media.

Inocula for the hydrogen measurements were prepared by making 10-fold dilutions of a 24-h Trypticase soy broth culture (BBL) in sterile 0.05% peptone broth and adding 3 ml of appropriate dilutions of 27 ml to phenol red broth base with 1.0% glucose (Difco) prewarmed to 35° C. In a limited number of tests, members of the coliform group were tested in lauryl tryptose broth (Difco). Viable counts were made by spreading appropriate dilutions from the 10-fold series on TSA and counting colonies after 35 h of incubation at 35° C. Viable counts were also made on each organism at the time of hydrogen evolution and at the end of 24 h of incubation.

Hydrogen measurements

The experimental apparatus for measuring hydrogen evolution by the test organisms consisted of a test tube (25 by 90 mm) containing two electrodes plus broth and organisms and positioned in a 35° C. water bath. Leads from the electrodes were connected to a dc buffer amplifier (type 122, Neff, Inc., Duarte, Calif.) which in turn was connected to a strip chart recorder (model 194, Honeywell Industrial Div., Fort Washington, Pa.). The dc buffer amplifier served to match the high impedence of the electrode test system with the strip-chart recorder. Hydrogen evolution was measured by an increase in voltage in the negative (cathodic) direction and was recorded on the strip-chart recorder.

The electrodes employed in the apparatus were a standard calomel (SCE-Beckman Instruments Inc., Fullerton, Calif.) as the reference electrode cemented to a plastic cap and a platinum electrode was formed by shaping a strip of platinum to fit the circumference of the test tube; a section of the platinum was positioned outside of a test tube for attachment to the amplifier lead. During operation, the platinum electrode and test tube were steam-sterilized by conventional autoclave procedures. The reference electrode (SCE) attached to the plastic cap, was sterilized by exposure for 30 minutes to two ultraviolet lamps (15T8, General Electric Heights, Ohio) housed in a clear plastic box. A number of tests demonstrated this technique to be effective in sterilizing the reference electrodes.

Figure 8:
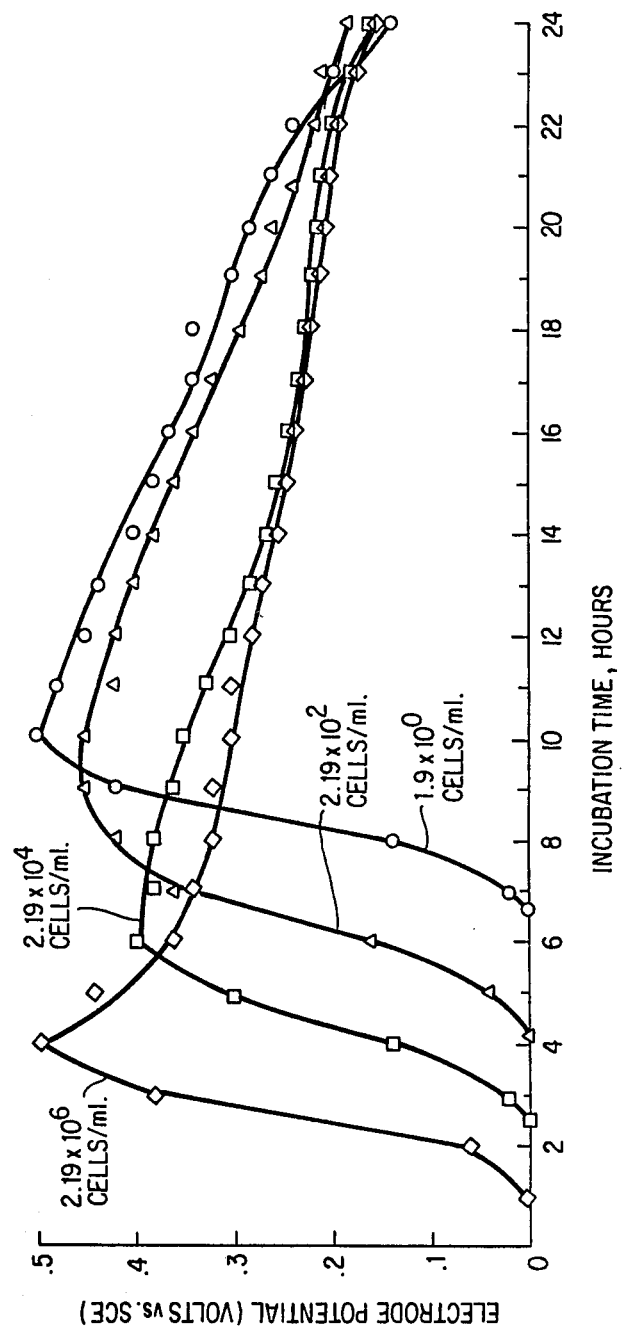
FIG. 8 is a strip chart recording of a series of cultures of $E.$ $coil$ wherein the bacterial concentration of the initial inocula in each sample was varied.

The strip chart recording of the millivolt response curve for $1.9 \times 10^9$ cells of *E. coli* per milliliter is shown in FIG. 8. Characteristically, for hydrogen producing organisms, the recording shows a lag period during which the microorganism is growing but is present in insufficient populations to give a response. Once the microorganism population has reached a sufficient level, a response is noted which is attributable to the microorganism. As the amount of hydrogen evolved becomes sufficient, the electrode response characteristics rapidly change as noted by the sudden increase in potential. The period of decline after the maximum potential was reached (400 to 500 millivolts) occurred over a 3 to 4 hour period.

The relationship between inoculum size and length of the lag period for various inocula of *E. coli* is shown in FIG. 8. Lag times ranged from 1 hour for $10^6$ cells/ml to 7 hours for $10^0$ cells/ml which indicated (1) that each 10-fold increment of cells reduced the lag time by 60 to 70 minutes and (2) that the mean cell concentration at time of rapid buildup in hydrogen was $1 \times 10^6$ cells/ml. Because initial studies showed no differences in the response curves for washed or unwashed cells, these studies were conducted with unwashed cells. In addition, no differences in response curves or lag times were noted from coliforms, *E. coli*, *E. aerogenes*, and *C. intermedium*, when tested in lauryl tyrptose or phenol red broth supplemented with glucose. Gas charomatographic analysis of headspace gas showed that for the cultures used in this study, the level of $H_2$ for 24 h cultures was between 4 and 10% by volume. The only exception was *S. marcescens* in which $H_2$ was estimated as a trace ($\leq 1\%$). Limited studies indicated that pH did not change markedly before or during the time $H_2$ was detected.

EXAMPLE 2

Figure 10:
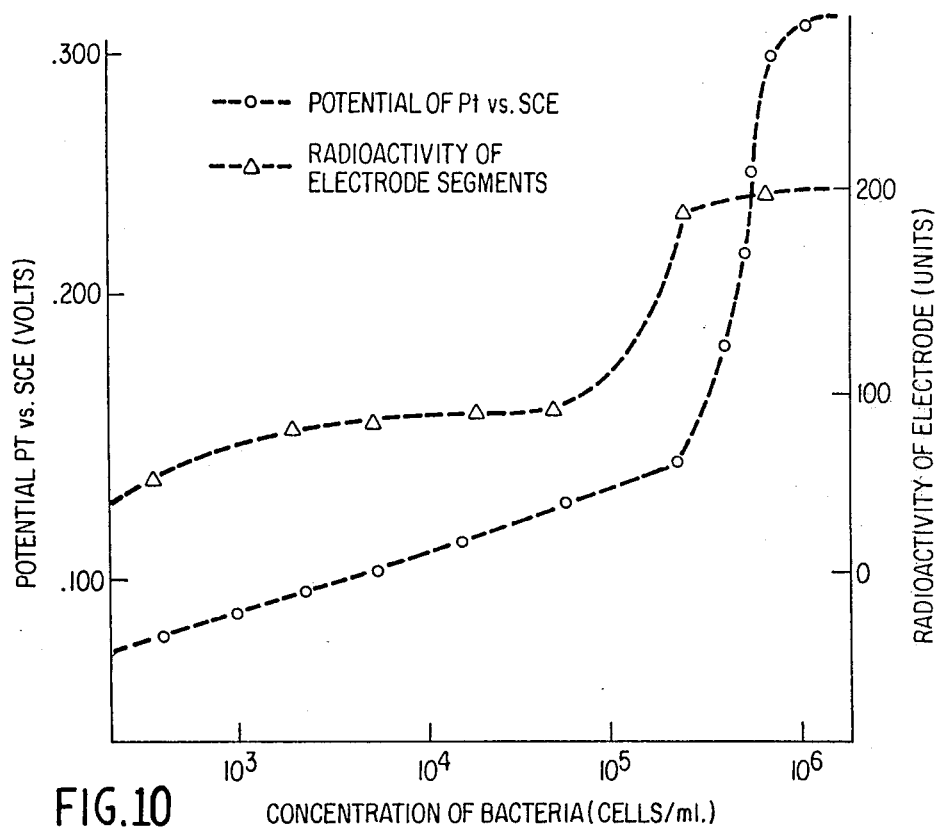
FIG. 10 is a correlation diagram of potential and radioactivity at the measuring electrode as a function of cell concentration for radioactive alkalescens in TSB media.
Figure 11:
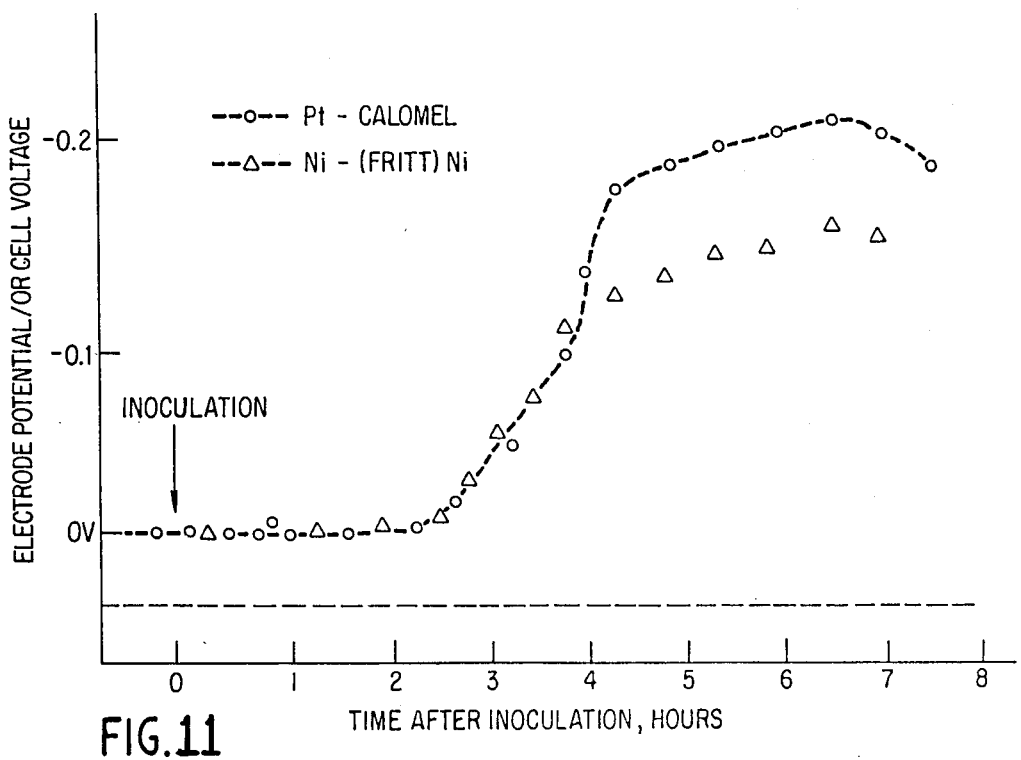
FIG. 11 shows two plots of potential versus time obtained from a platinum wire-calomel electrode system and a nickel-nickel electrode system in the same TSB culture medium of alkalescens; the nickel electrodes are positioned as in FIG. 3.

FIG. 10 shows a comparison of the potential characteristics of a hydrogen producing bacterium (*E. coli*) and a nonhydrogen producing bacterium (Alkalscens). Each bacterium was cultivated in a broth medium of lauryl tryptose glucose by inoculating each medium with 1 ml of sample containing 100 cells/ml. The response characteristics were measured by a platinum-calomel electrode couple. The recordings show the much greater response characteristics in the system containing the hydrogen producing bacteria compared to the response characteristics of the non-hydrogen producing bacteria. Note that the same lag time is observed when the initial inoculum and growth rates are the same.

EXAMPLE 3

The data in FIG. 10 provide a correlation which show that the change in potential of a culture medium of alkalescens as a function of cell concentration. A 1 ml sample of radioactive alkalescens (initial innoculum size 100 cells/ml) was cultured in a 10 ml Trypticase soy broth medium at 37° C. Each time a potential reading was made, a sample of the electrode was taken and measured for radioactivity. The plots clearly indicate corresponding increases in potential and radioactivity as a function of cell concentration. The data clearly indicate that the cells increasingly concentrate about the surface of the electrode and that the potential response is caused by this build-up of cells about the electrode.

EXAMPLE 4

A 1 ml sample of alkalescens was cultured in 10 ml of Trypticase soy broth medium for 7 hours. The growth of the bacterium was monitored at the same time by two different electrode systems, i.e., a platinum wire-calomel system and a nickel-nickel system in which one nickel electrode was shielded from organisms by a glass frit. As can be ascertained by reference to FIG. 11, both curves obtained are essentially the same except that the nickel-nickel electrode system does not appear to be quite as sensitive as the platinum-calomel system.

EXAMPLE 5

A 1 ml sample of *Pseudomonas aerogenosa* was cultured in trypticase soy broth in a cell described in FIG. 3 in which both the measurement and reference electrodes were type 3 or 4 stainless steel. The shielding material in this example was peptone agar with 10 mg/ml NaCl. When the cell population of $9 \times 10^4$ cells/ml was reached, the potential change was detected as shown in FIG. 1.

EXAMPLE 6

The same procedure described in Example 5 was followed with the exception that the organism cultured was *E. coli* in a medium of Trypticase soy broth. A potential reading was observed at a population level of $1.2 \times 10^5$ cells/ml.

EXAMPLE 7

The same procedure of Examples 5 and 6 was followed with the exception that the growth medium was sodium glycolate medium and the organism was *Shigella alkalescens*. A potential reading was observed at a population level of $8.6 \times 10^4$ cells/ml.

EXAMPLE 8

The same procedure of Examples 5–7 was followed except that the growth medium was sodium glycolate $+0.5$ ml of human blood and the organism was *Hemophilus influenzae*. A potential reading was observed at a population level of $2.4 \times 10^5$ cells/ml.

EXAMPLE 9

The same procedure of Examples 5–8 was followed except that the organism was *Bacillus subtilus* in 1% nutrient broth with 0.5% NaCl at 30° C. A potential reading was observed at a population level of $2.3 \times 10^3$ cells/ml.

EXAMPLE 10

The same procedure of Examples 5–9 was followed except that the organism was *Candida tropicanas* and the growth medium was 10% nutrient broth with 30% dextrose at 30° C. Detection was at $3.1 \times 10^5$ cells/ml.

EXAMPLE 11

The cell of FIG. 4 was used to culture the fungus *Asperigullus niger* in Trypticase soy broth at 25° C. A potential reading was observed at a population level of $10^4$ cells/ml.

EXAMPLE 12

A culture of *Pseudomonas aeroginosa* was washed in non-nutrient buffer (Phosphate buffer solution or PBS) and "starved" at 15° C. for 48 hours. Cells maintained in this condition are not dividing or metabolizing but are technically alive. Therefore they still have a net negative charge. These cells were then added to a cell described in FIG. 4 with stainless steel electrodes but the nutrient broth was replaced with PBS. At a population of $2 \times 10^5$ viable cells/ml a signal was observed.

EXAMPLE 13

Two samples of bovine milk were added to cells of the type described in FIG. 3. One sample was Pasteurized and one was "raw" milk. The milk served both as a growth medium and inoculum in both cases. The electrodes were stainless steel and the membrane was saline agar. The experiment was conducted at a temperature of 37° C. Each sample produced a signal at around $10^5$ cells/ml but the "raw" milk developed the signal in 2 and ½ hours whereby the Pasteurized milk reached $10^5$ cells and gave a signal at 4 and ½ hours.

EXAMPLE 14

Antimicrobial Susceptibility Tests

Reagents and Media

Identical lots of media and antimicrobial agents were used in the susceptibility tests performed. The media used were trypticase soy agar (TSA) and TSB from Baltimore Biological Laboratories (BBL), Cockeysville, Maryland. The 12 antimicrobial agents used in the experiments, which were chosen on the basis of their clinical usefulness, were laboratory reference standards including the following antibiotics: penicillin G potassium, caphalothin sodium, tobramycin, vancomycin hydrochloride and streptomycin sulfate obtained from Eli Lilly and Co.; tetracycline and carbenicillin obtained from Pfizer Laboratories; ampicillin and sodium nafcillin from Wyeth Laboratories; kanamycin and methicillin from Bristol Laboratories; gentamicin from Schering.

The action of an antibacterial drum against a susceptible bacterium is either bacteriostatic or bactericidal. A bacteriostatic agent merely inhibits bacterial growth, an effect which is reversible upon removal of the antimicrobial agent. Bactericidal agents produce an irreversible, killing effect on the microorganism susceptible to the drug. Of the 12 antibiotics, all are bactericidal with the exception of tetracycline which is bacteriostatic. Penicillin G, ampicillin, nafcillin, methicillin, and carbenicillin all belong to the penicillin family and as such their mode of action involves interference with the synthesis of cell walls of bacteria. This is also true of cephalothin, a cephalosporin, and vancomycin, a glycopeptide. The aminoglycoside antibiotics kanamycin, streptomycin, and gentamicin cause specific misreadings of the genetic code at the ribosomal level, thereby interfering with the protein synthesis of the bacterium. This also results from the use of tetracycline, which specifically prevents attachment of amino acid activated transfer RNA to the ribosomes.

Cultures

The following cultures were obtained from Hoffmann-LaRoche, Inc. and were derived from the American Type Culture Collection (ATCC) organisms as indicated: *Escherichia coli*, "Seattle Strain" ATCC 25922, *Klebsiella pneumoniae* ATCC 27736; *Pseudomonas aeruginosa*, ATCC 9721. These bacteria are gram negative bacteria. The following bacteria are gram positive: *Staphylococcus aureus*, "Seattle Strain" ATCC 25923; *Staphylococcus epiderdimis* ATCC 14990; and *Streptococcus pyogenes*, ATCC 10389. In addition, clinical specimens of these same six organisms were obtained from sensitivity isolates from the University of Virginia Hospital Department of Clinical Pathology Bacteriology Section. These organisms, both pathogenic and non-pathogenic (*Staphylococcus epidermidis*), were chosen because they are some of the most frequently encountered organisms in clinical isolates.

Inoculum Preparation and Viable Counts

Inocula were prepared by making a 100-fold dilution×2 of an overnight TSB culture of the organism to be tested in sterile TSB prewarmed to 35° C. Thus, the total dilution of overnight stock was $10^{-4}$. From the $10^{-4}$ series, 0.3 ml was transferred to a test tube (Falcon, disposable #2057) containing 2.7 ml of TSB if the growth control, or 2.6 ml of TSB plus 0.1 ml of a particular concentration of an appropriate antibiotic to be tested. The antibiotic was weighed on an analytical balance, according to each agent's activity standard, and diluted with sterile distilled water in a volumetric flask to achieve a stock solution of 1000 mcg/ml which was then frozen in small aliquots. Further dilutions as necessary for susceptibility testing were also achieved through the addition of sterile distilled water to this stock concentration. Viable counts were made by plating appropriate dilutions from the $10^{-4}$ series on TSA and counting colonies after 24 hours incubation at 35° C. Viable counts were also made on each microorganism at the time of MDC and again at the end of the 24 hour test period to confirm the minimum inhibitory concentration (MIC).

The experimental apparatus used in this study to monitor the inhibition of growth due to the addition of antibiotics consisted of test tubes, up to and including 8, size 17×100 mm, each containing a sterilized (by boiling) Pt-SCE combination electrode (Sargent-Welch, S-30101-15), plus TSB, microorganisms, and antibiotic where appropriate, positioned in a 35° C. heating block. Leads from the electrode were connected to a high impedance (greater than $10^8$ ohms) potentiometer, or voltage following device, which in turn was connected to a strip chart recorder (Hewlett-Packard type 680M). Microbial growth was measured by an increase in voltage in the negative direction with time as recorded on the strip chart recorder.

Figure 13:
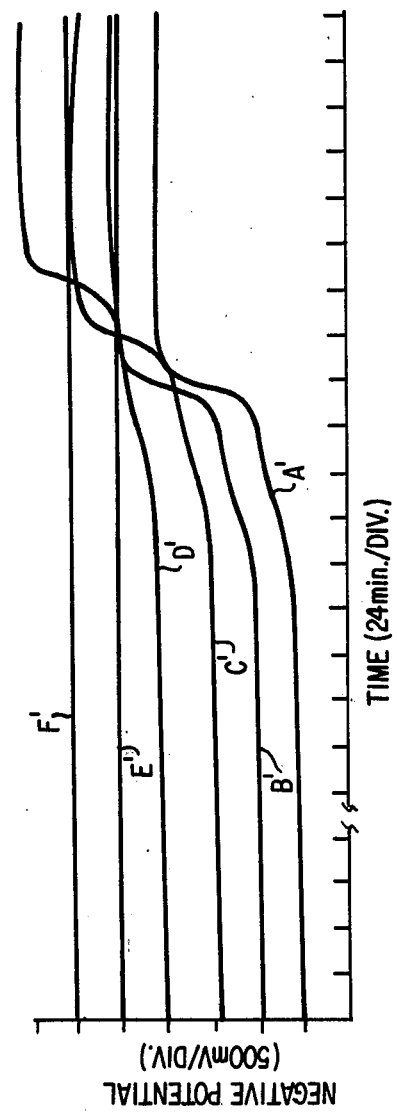
FIG. 13 shows several potential versus time curves which show the growth impeding influence of cephalothin on $K.$ $pneumoniae.$

FIG. 12 is a stripchart recording of the antimicrobial response curve of a four channeled experiment involving a clinical specimen of the non-hydrogen producing, Gram-positive bacteria *Staphylococcus epidermidis* treated with 0.012, 0.5 and 1.0 mcg/ml of the antibiotic ampicillin as shown in curves B, C and D respectively. Curve A shows the response curve of a control sample of *S. epidermidis* which has not been treated with ampicillin. FIG. 13 is a strip chart recording of the antimicrobial response curve of a six channeled experiment involving an ATCC culture sample of the pathogenic hydrogen producing, Gram-negative bacteria *Klebsiella pneumoniae* treated with 0.3, 0.4, 0.5 and 1.0 and 2.0 mcg/ml of cephalothin as shown in curves B', C', D', E' and F' respectively. Curve A' shows the response curve of a control sample of *K. pneumoniae* which has not been treated with cephalothin. Both figures show that the growth of the respective bacteria is increasingly inhibited by the particular antibiotic material used. The minimun inhibitory concentration (MIC) is defined as that amount of antimicrobial agent which totally inhibits the growth of the microorganism being tested. Tables 3 and 4 below show the MIC values of various antibiotics for a number of microorganisms as determined by the method of the present invention.

TABLE 3

ELECTROANALYTICALLY DETERMINED MIC VALUES/GRAM-NEGATIVE BACTERIA

| Organism | Antibiotic: concentration in mcg/ml | | | | | | | |
|---|---|---|---|---|---|---|---|---|
| | Amp | Carb | Ceph | Tetra | Kana | Genta | Strep | Tobra |
| *E. coli* (ATCC) | 4.0 | 4.0 | 8.0 | 1.0 | 3.0 | 0.5 | 9.0 | — |
| *E. coli* (clinical) | 6.0 | 5.0 | 9.0 | 4.0 | 4.0 | 1.0 | 9.0 | — |
| *K. pneumoniae* (ATCC) | 32 | >128 | 1.0 | 5.0–6.0 | 3.0 | 0.5 | 5.0–6.0 | — |
| *K. pneumoniae* (clinical) | — | >128 | — | 5.0–6.0 | 4.0 | 0.5 | 6.0 | — |
| *P. aeruginosa* (ATCC) | >128 | 64 | >360 | 64 | 32–64 | 2.0 | — | 4.0 |
| *P. aeruginosa* (clinical) | >128 | 64 | >360 | 64 | 64 | 4.0 | — | 8.0 |

TABLE 4

ELECTROANALYTICALLY DETERMINED MIC VALUES/GRAM-POSITIVE BACTERIA

| Organism | Antibiotic: concentration in mcg/ml | | | | | | | | |
|---|---|---|---|---|---|---|---|---|---|
| | Pen G | Amp | Naf | Meth | Ceph | Tetra | Vanco | Kana | Strep |
| *S. aureus* (ATCC) | .05 | .12–0.6 | .5 | .7 | .15–0.2 | 2.0 | 1.0 | .2 | 8.0 |
| *S. aureua* (clinical) | .05 | .12 | .5 | .7 | .8–1.6 | 2.0 | 2.0 | .5–1.0 | 8.0 |
| *S. epidermidis* (ATCC) | .08–0.1 | 1.0 | .5–1.0 | .5–1.0 | .1 | 1.0–2.0 | 1.5 | .4 | 4.0 |
| *S. epidermidis* (clinical) | .1 | 0.8–1.0 | .5–1.0 | .5–1.0 | .5–1.0 | 2.0 | 2.0–3.0 | .6 | 4.0–6.0 |
| *S. pyogenes* (ATCC) | — | — | — | — | — | — | .1–.5 | | .1 |
| *S. pyogenes* (clinical) | — | — | — | — | — | — | .5 | | .1 |

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. An apparatus for the electrochemical detection of living microorganisms in a fluid medium, which comprises: a chamber having an inlet means for introducing a fluid sample of a microorganism therein and containing a fluid growth medium suitable for the culturing of microorganisms; means attached to said chamber for drawing a vacuum within said chamber; means for sealing said inlet means which means is self-sealing after having been punctured by a means for delivering a microorganism-containing sample to said chamber; measuring electrode means fixedly attached to the exterior of said chamber, one end of which penetrates through said chamber into the interior thereof and is in contact with said fluid growth medium, about which accumulates said microorganisms thereby setting up a charge-charge interaction at said electrode, said electrode being responsive to said charge-charge interaction established at the electrode; reference electrode means fixedly attached to the exterior of said chamber, one end of which protrudes into the interior of said chamber and which is covered with a fluid growth medium permeable shielding means that prevents contact of said reference electrode with said microorganisms, said reference electrode in corporation with said measuring electrode establishing the potential of said electrochemical apparatus; and a potentiometer having an input impedance of $10^7$ to $10^{10}$ ohms which is conductively connected to said measuring and reference electrodes.

2. The apparatus of claim 1, wherein said measuring electrode and said reference electrode are fabricated of the same metal.

3. The apparatus of claim 2, wherein said electrodes are fabricated from stainless steel.

4. The apparatus of claim 1, wherein said shielding means is a gel.

5. The apparatus of claim 4, wherein said gel is agar gel.

6. The apparatus of claim 1, wherein said inlet means and vacuum means are attached and secured to said chamber.

7. The apparatus of claim 1, wherein said inlet means and vacuum means are attached and secured to said sealing means.

8. An apparatus for the electrochemical detection of microorganisms in a fluid medium, which comprises:
a chamber closed at one end and open at the other end thereof and containing a fluid growth medium suitable for the culturing of microorganisms;
measuring electrode means fixedly attached to the exterior of said chamber one end of which protrudes through said chamber into the interior thereof and is in contact with said fluid growth medium about which accumulates said microorganisms thereby setting up a charge-charge interaction at said electrode, said electrode being responsive to said charge-charge interaction established at the electrode;
reference electrode means fixedly attached to the exterior of said chamber, one end of which protrudes into the interior of said chamber and which is covered with a fluid growth medium permeable shielding means that prevents contact of said reference electrode with said microorganisms for establishing the potential of said cell in cooperation with said measuring electrode;
conduit means penetrating through the base of said chamber and said shielding means such that the internally protruding open end thereof is exposed to said fluid culture medium for transport of material into said chamber;
plunger means fitting within said open end of said chamber which moves freely inwardly and outwardly which allows a sample containing said microorganisms to be withdrawn into or expelled from said chamber through said conduit; and
a potentiometer having an input impedance of $10^7$ to $10^{10}$ ohms which is conductively connected to said measuring and reference electrode.

9. An apparatus for the electrochemical detection of living microorganisms in a fluid medium; which comprises:
a conduit containing a hollow bore therethrough and having a fluid sampling end;
a conductive lead attached to and in conductive communication with said conduit so that said conduit functions as a measuring electrode which responds to the charge-charge interaction set up by accumulation of said microorganisms about said electrode;
insulator means concentrically disposed within the bore of said conduit and having an interior bore running therethrough;
a second conductive lead disposed throughout the length of said interior bore which traverses said insulator means;
means for attaching the end of said second conductive lead at said fluid sampling end of said conduit to said insulator which attaching means is impervious to the microorganisms within said fluid medium but which is permeable to said fluid medium; and
a potentiometer having an input impedance of $10^7$ to $10^{10}$ ohms which is conductively connected to said measuring electrode and to said second conductive lead.

* * * * *